United States Patent
Urban et al.

(10) Patent No.: US 8,532,364 B2
(45) Date of Patent: Sep. 10, 2013

(54) APPARATUS AND METHOD FOR DETECTING DEFECTS IN WAFER MANUFACTURING

(75) Inventors: Alexander Urban, Attenkirchen (DE); Peter Schaeffler, Essenbach (DE); Andreas Pfeiffer, Marzling (DE); Holger Schwekendiek, Freising (DE)

(73) Assignee: Texas Instruments Deutschland GmbH, Freising (DE)

( * ) Notice: Subject to any disclaimer, the term of this patent is extended or adjusted under 35 U.S.C. 154(b) by 325 days.

(21) Appl. No.: 12/704,383

(22) Filed: Feb. 11, 2010

(65) Prior Publication Data
US 2010/0208980 A1   Aug. 19, 2010

(30) Foreign Application Priority Data

Feb. 18, 2009  (DE) .......................... 10 2009 009 355
Feb. 18, 2009  (DE) .......................... 10 2009 009 356

(51) Int. Cl.
*G06K 9/00* (2006.01)
(52) U.S. Cl.
USPC ............... 382/149; 356/237.2; 356/237.6; 356/600; 356/640; 250/559.42
(58) Field of Classification Search
USPC ................. 382/149, 141; 356/237.2–237.6, 356/600–640
See application file for complete search history.

(56) References Cited

U.S. PATENT DOCUMENTS

| | | | |
|---|---|---|---|
| 4,575,244 A * | 3/1986 | Kaffka et al. | 356/343 |
| 7,106,432 B1 * | 9/2006 | Mapoles et al. | 356/237.2 |
| 7,872,754 B2 * | 1/2011 | Wadman | 356/445 |
| 2006/0180775 A1 | 8/2006 | Paradis | |

FOREIGN PATENT DOCUMENTS

| | | |
|---|---|---|
| DE | 4413832 | 5/2000 |
| DE | 102006017833 | 10/2008 |
| EP | 1637868 | 3/2006 |
| WO | WO 03002984 | 1/2003 |

\* cited by examiner

*Primary Examiner* — Tarifur Chowdhury
*Assistant Examiner* — Isiaka Akanbi
(74) *Attorney, Agent, or Firm* — Warren L. Franz; Wade J. Brady, III; Frederick J. Telecky, Jr.

(57) ABSTRACT

Apparatus for inspecting a semiconductor wafer (8) has a plurality of light sensors (2) arranged relative to a light source (1) and wafer inspection platform (4), so that images of different angle views of a surface of the wafer can be received and compared with corresponding images taken of a reference wafer to automatically detect defects based on image comparison. The light sensors (2) may receive superposed images of light (7) reflected directly from the light source (1) off the wafer surface and light (6) indirectly reflected off the wafer surface after first reflecting off a dome (3) with a diffusely reflecting inner surface (5) positioned over the platform (4).

16 Claims, 5 Drawing Sheets

APPARATUS AND METHOD FOR DETECTING DEFECTS IN WAFER MANUFACTURING

This application claims priority under 35 USC 119 of German Patent Application Nos. 10 2009 009 355.9 and 10 2009 009 356.7, both filed Feb. 18, 2009, the entireties of which are incorporated herein by reference.

BACKGROUND

The invention relates to an apparatus and a method for detecting defects in wafer manufacturing.

Macroinspection tools are used in semiconductor manufacturing environments in order to detect deficiencies or failure early in the production process. Many macroinspection systems are scanner based. Macroinspection assistants are used to detect color changing defects (focus, spin problems, etc.), topography related defects (scratch, particle, etc.) and other defects such as, for example, underexposure, shutter blade problems, particle on chuck defects, small defocus, spot defects. However, known systems approaches are expensive and lack flexibility. Furthermore, different types of defects require different inspection tools as the defect types are conflictive.

SUMMARY

It is an object of the invention to provide and apparatus and a method for detecting defects on a wafer that is capable of detecting all kinds of defects.

Accordingly, an apparatus for inspecting a semiconductor wafer is provided. The apparatus includes a light source and a plurality of light image sensors arranged relative to each other and to a plane, so that the light sensors can simultaneously acquire images from different angles of the surface of a first wafer placed for inspection at the plane. A data processing unit is adapted to receive the images from the light sensors, to individually compare each image with an image previously taken of a second wafer using the same light sensor, and to automatically detect a defect based on the image comparison. The data processing unit can be advantageously adapted to detect a defect requiring soft light and a defect requiring hard light. The light sensor may be a camera and the images may be regarded as pictures of the wafer surface.

In an embodiment, the apparatus may include a dome having an inner surface. The dome may be arranged relative to the light source, the plurality of light image sensors and the plane so that the image sensors can receive light from the light source that is reflected by the inner surface of the dome and subsequently by a surface of the semiconductor wafer. This is a very efficient way of detecting multiple different defects usually requiring a hard light and a soft light illumination. Furthermore, this aspect of the invention provides an apparatus for inspecting a semiconductor wafer that is mobile and can be implemented in conjunction with any type of semiconductor manufacturing equipment.

According to another aspect of the invention, an apparatus for inspecting a semi-conductor wafer comprises a light sensor, a dome with an inner surface directed towards a plane at which a semiconductor wafer is placed for inspection, and a light source for illuminating the inner surface of the dome and the semiconductor wafer. The light sensor is arranged relative to the dome, the light source and the semiconductor wafer, so as to receive light from the light source that is first reflected by the inner surface of the dome and subsequently by a surface of the semiconductor wafer. The light sensor also receives light that is directly reflected from the wafer surface (i.e., without reflection from the inner surface of the dome). The dome has an inner surface that is configured to be diffusely reflecting. The light sensor receives an overlaid image of reflected light from the wafer surface with and without interaction of the inner surface of the dome. Using the dome in the above manner provides that all relevant defects can be detected with one or more light sensors.

The inner surface may advantageously be configured to have an effect that corresponds to the reflection of a gray surface to light incident from a white light source. This is based on the recognition that the primary difference between a gray surface and a mirrored surface is one of diffused versus specular reflection. Specular reflection off the inner surface of the dome may then be advantageously avoided. The directly reflected light from the wafer surface and indirect light from the inner surface of the dome advantageously overlays at the light sensor.

The defects that can be detected are defects which require hard light and soft light. These defects are for example, spin-on glass defects and scratches which need hard light from a side (flat incident angle of the light) and color changing defects (focus, spin problems) which need soft light from all sides. Further defects which can be detected are shutter blade problems, underexposure, particles on chuck, small defocus, particle defects, spot defects, spin defects, and/or large spots.

The inner surface of the dome may advantageously be configured to absorb light uniformly across the spectrum of the light source. The dome may then have a diffusely reflecting surface that absorbs more or less uniformly across the spectrum. It may reflect a bit less than a white surface for white light and so appear matte gray for light incident from a white light source. Depending on the strength of the light source and the characteristics of the light sensor, the surface may be configured to absorb more or less light and may therefore have the effect of a surface that appears lighter or darker gray for light incident from a white light source.

A light source with a distribution of energy that is not effectively uniform across the spectrum appears colored. However, even with colored light, the interaction of the light source and dome may be similar to the effect of a white light source and a gray inner surface of the dome. The invention is therefore not limited to a gray inner surface of the dome and a white light source but to the effect of dome and light source for the image received with the light sensor. A light beam with a particular energy distribution may appear colored but this may be compensated so that effectively the reflection is that of a white light source and a gray surface.

The shape of the dome may be convex. The dome may extend beyond the circumference of the surface of the wafer to be inspected. The inner surface of the dome is such that the light from a light source which is configured to illuminate the surface of the wafer is neither completely absorbed nor completely reflected from the inner surface of the dome. For white light, the inner surface of the dome should preferably be other than completely black or white.

There are many ways of configuring the inner surface in terms of color and the structure of the surface. However, in an embodiment it may be advantageously adapted to diffusely reflect a certain amount of the light within the dome in order to achieve a diffuse (and/or even) illumination of the wafer from all sides. Additionally, a certain amount of light should normally be reflected from the wafer surface directly to the light sensor. Therefore, the light sensor receives an overlay of two effects, one of which is diffuse illumination of the wafer surface and the other a direct reflection of light from the light source by the wafer surface. This allows detection of defects which require hard light and defects which require soft light. For example, color changing defects (focus or spin problems) require soft light from all sides and topography related defects (scratch, particles etc.) require hard light from one side.

The inner surface of the dome may be adapted to reflect the light of the light source by more than 10% and less than 90%. For a light source which emits substantially white light, the inner surface may be gray having a ratio of black and white of between 30% white and 70% black and 30% black and 70% white. The inner surface may advantageously have gray color of 50% black and 50% white. In other words, the inner surface is adapted to reflect light from the light source and/or from the surface of the wafer in a diffuse manner. In other words, the inner surface may be configured to reflect less than a white surface and more than black surface. Furthermore, the inner surface can be configured to reflect between 70% and 80% of the light from the light source. Configurations with slightly different values may still achieve the advantageous effects of the invention.

In an aspect of the invention, the light source emits white light and the inner surface of the dome is adapted to partially absorb light so that white light is diffusely reflected from it.

In one embodiment, the light source may have a circular shape. It may, for example, be a circular neon lamp. This can provide a suitable even illumination of the wafer from all sides along its circumference. The light source may have a diameter so as to substantially encompass the outer circumference of the semiconductor wafer. A cross section of the inner surface of the dome may have a circular or parabolic shape. This provides efficient reflection. The light sensor may be arranged at the dome so as to have a maximum distance from the surface of the semiconductor wafer to be inspected. In an embodiment, the light sensor may be arranged in a top center of the dome. The light source may advantageously be arranged between the light sensor and the inspection plane at which the wafer is to be placed for inspection. The light source may be arranged between the lower edge of the dome and the wafer. The lower edge of the dome directed towards the wafer may also have a circular shape substantially encompassing the wafer and the light source.

The light sensors may be coupled to a dome and configured to receive light from inside the dome. A light sensor may be arranged in the top center of the dome. The dome and the light source may be configured as set out above. In particular, the inner surface of the dome and the light source may interact so as to have an effect similar to a white light source and a matte gray inner surface with respect to an image taken with the light sensor. In an embodiment, the light source may be a white light source and the inner surface may be gray.

The invention also provides a method of detecting a defect on a semiconductor wafer. A surface of a first wafer is illuminated. A plurality of images of the surface of the first wafer is acquired from different angles (for example simultaneously, i.e., without moving the wafer). A surface of a second wafer is then illuminated and a plurality of images of the surface of the second wafer can be acquired from different angles. The images of the first wafer can be compared with images of the second wafer taken at corresponding angles.

A surface of the wafer may be illuminated with a light source. The light may then be diffusely reflected at an inner surface of a dome and also reflected from the surface of the wafer. An image may then be taken of the reflected light with a light sensor.

In another aspect, a method of detecting a defect on a semiconductor wafer is provided. The semiconductor wafer is illuminated with light from a light source in a manner that the light of the light source is diffusely reflected at an inner surface of the dome. Light reflected from the dome is reflected from the surface of the wafer towards a light sensor. The light sensor also receives light from the wafer, which is direct light from the light source. The light sensor may then take an image of an overlay of direct light and indirect light.

According to another aspect, a surface of a first wafer may be illuminated and a plurality of images of the surface of the first wafer from different angles may be simultaneously acquired. A surface of a second wafer may be illuminated and a plurality of images of the surface of the second wafer from different angles may be acquired. Finally, images of the first wafer may be compared with images of the second wafer. In an advantageous embodiment, an apparatus may be provided with a dome, a light source and a light sensor in accordance with the aspects set out above. The evaluation may then be performed by comparing images taken with the light sensor from previous wafers with images taken from subsequent wafers. The evaluation can be performed by using only images from consecutive wafers. Using a template or reference image may then be avoided. This simplifies the process of detecting defects.

BRIEF DESCRIPTION OF DRAWINGS

Further aspects of the invention will become apparent from the following description of example embodiments taken with reference to the accompanying drawings, wherein.

DETAILED DESCRIPTION OF EXAMPLE EMBODIMENTS

Figure 1:
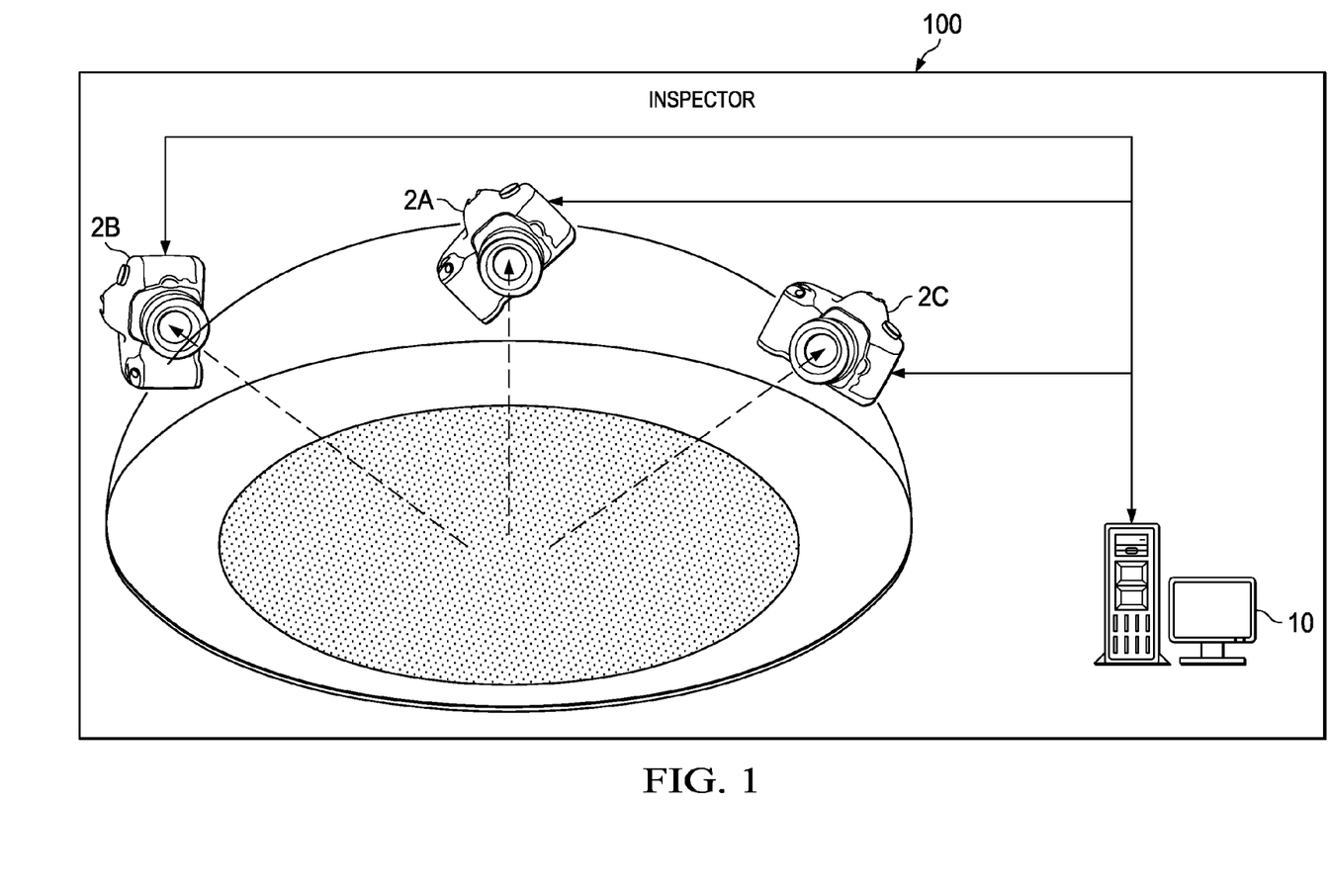
FIG. 1 shows a simplified diagram of an embodiment of the invention including a processing unit.

FIG. 1 illustrates data processing in an inspection system 100 of the images taken with a plurality of light sensors 2A, 2B and 2C. The light sensor 2A, 2B and 2C may be CCD cameras with moderate resolution. In some embodiments, the CCD cameras may have 3, 5, 8, 10, 12, 20 or more Megapixels. All light sensors may take an image at the same time for the same wafer. The images are passed to processing unit 10, which can be, for example, a personal computer, workstation, etc. The images from the light sensors 2A, 2B, 2C may then be analyzed individually so as to detect defects.

A defect may then be detected automatically by comparing a current image overlaid with a reference image. A difference image may then be calculated for each pixel of the overlaid current and reference images. In an advantageous embodiment, the reference image is the image of a previous wafer which has been monitored before. The previous wafer may be any wafer; so does not have to be an ideal wafer without defects. This simplifies the evaluation process, as no ideal template or reference is required.

Figure 2:
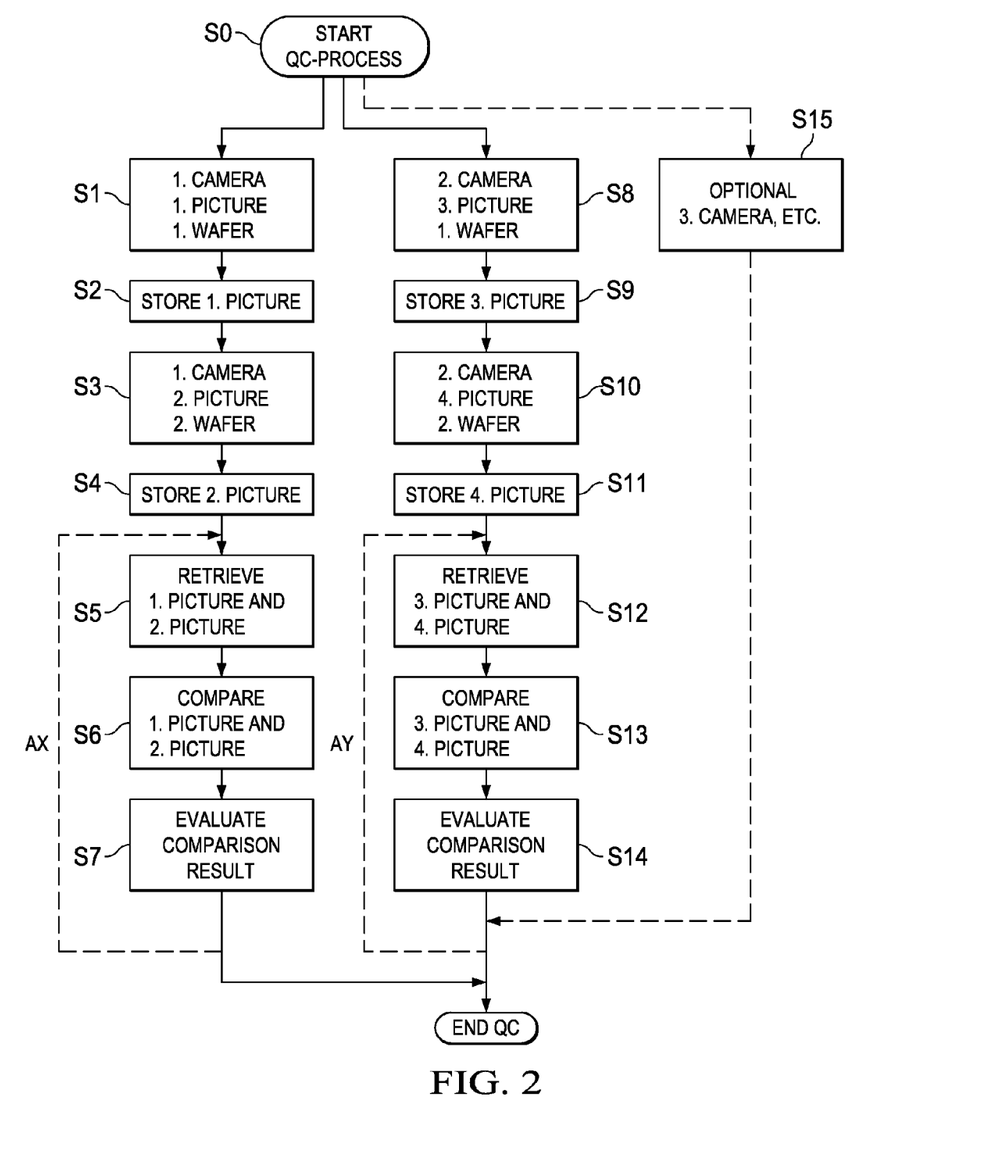
FIG. 2 shows a flow chart of aspects of the invention.

FIG. 2 shows a flow chart of an example wafer inspection process according to the invention. The quality control process starts in step S0. For example, one or more lots of wafers may be subject to quality control with the inspector 100. In step S1, a first image is taken from a first wafer. The first camera (or other light sensor) is fixed and has a fixed angle and position with respect to each wafer in the inspection system. The first image is then stored (step S2). A second image is then taken from a second wafer using the same first camera in the same position relative to the second wafer as before relative to the first wafer (step S3). This image is also stored (step S4). Both images are retrieved in step S5 and compared with each other in step S6. The comparison result is evaluated in step S7. Steps S8 to S14 are similar to steps S1 to S7, but they are performed with a different camera, i.e., a second camera having a different position (and thus different angle field of view) relative to the wafer surface. Steps S8 to S14 may be performed in parallel with steps S1 to S7 (i.e., with corresponding steps performed at the same time) or independently keeping the wafer in the same position to the two cameras. Furthermore, a third camera may be used at step S15 for optionally taking pictures of consecutively inspected wafers from another angle view using steps similar to those shown for steps S1 to S7 or S8 to S14 (indicated in FIG. 2 as a combined step S15). Further cameras may be used in the same manner as the first, second and third cameras. Advantageous implementations use consecutive images taken with the same camera or cameras from the same position relative to two different wafers consecutively inspected.

In an embodiment, the picture comparison procedure steps may be repeated for additional comparisons (steps S5 to S7; S12 to S14) using different parameters for detection of different defects, as indicated by the dashed line loops ΔX and ΔY. The process can also be repeated using additional images taken with the same different angled views of a third or additional wafers, and comparing the resulting images with one or more prior wafer images until, for example, all wafers of a lot have been checked.

Comparing the two images may be performed by determining the differences of both images. The wafers are advantageously wafers from the same production cycle or lot. This relates to the recognition that defects on wafers even from the same lot or production cycle do not have exactly the same defects. Therefore, it is possible to determine defects based on difference of two images of two consecutive wafers passed through the inspection system.

In an embodiment, the inspection system may advantageously be configured to automatically detect defects which require hard light and defects which require soft light. Examples of defects that can be detected include: at least one defect requiring hard light from one side, i.e., defects requiring a flat incident angle of the light (e.g., topography related defects, spin-on glass defects, scratches, particles); at least one defect requiring soft light from all sides (e.g., spot defects, underexposure, shutter blade problems, particle on chuck, defocus, and/or large spots, spin problems). This list is merely representative of the types of defects that can be detected, and other defects may also be detected.

Figure 3:
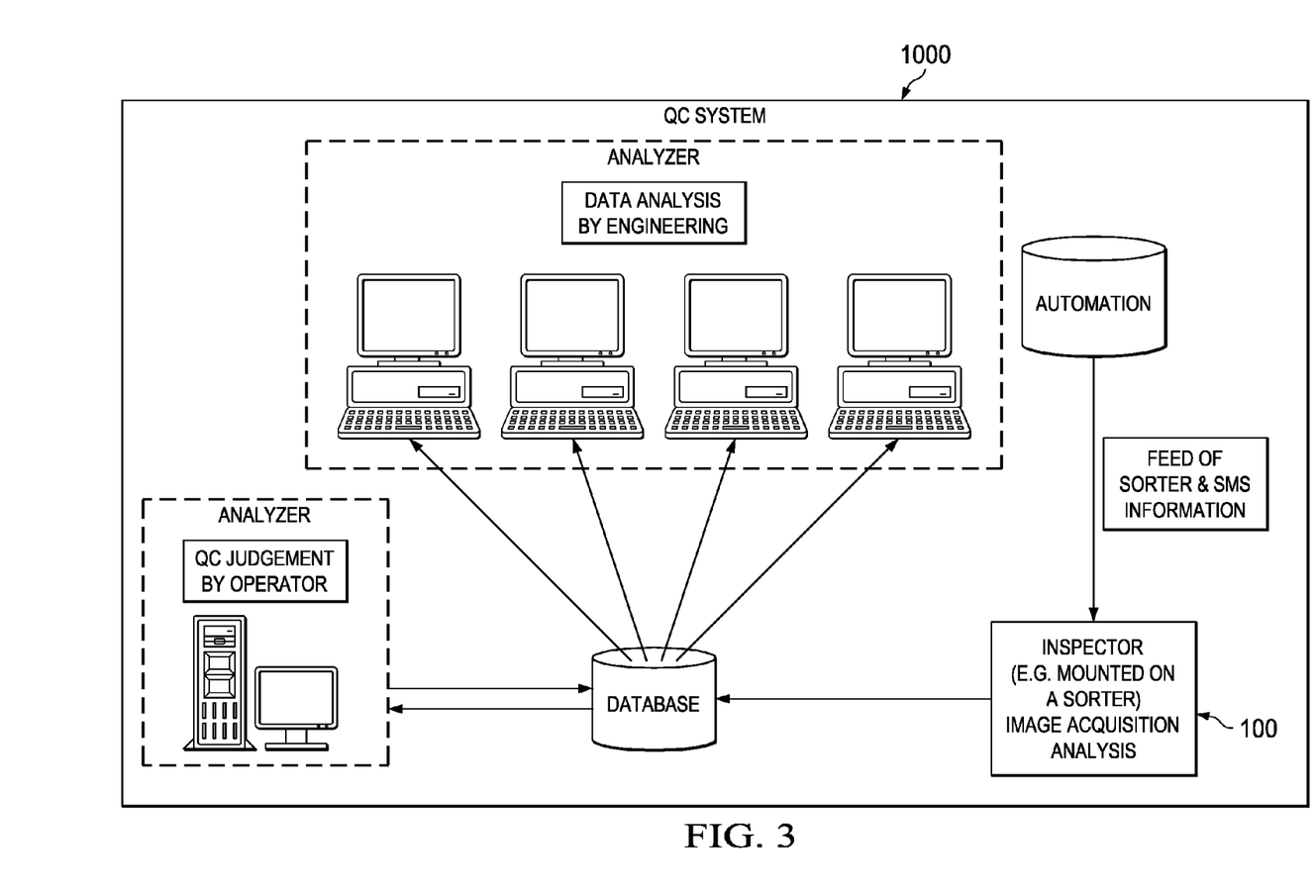
FIG. 3 shows a block diagram of a system according to the invention.

FIG. 3 shows a simplified block diagram of a quality control system 1000 including an inspection system 100. The inspection system 100 may be implemented in accordance with aspects of the invention. The inspection system may be mounted on a production tool and/or sorter. It is configured to perform image acquisition and image analysis of images taken from wafer surfaces as described above and below. The inspection system is configured to receive data from an automation system to allow a communication with the production tool and/or sorter as well as with a factory control system. The communication serves to address each picture taken in the inspection system with a wafer identification number (ID) as well as with other production information. (e.g., log point of inspection, tool name, etc.). Evaluation results (received, for example, as explained with respect to FIG. 3) may be transmitted to a database. The database can then be used for quality control (QC) judgment by an operator. Furthermore, the data can be used for further data analysis for engineering and product improvement. The results of the wafer inspection can be used to improve the produced wafers, to adapt the manufacturing procedure and to eliminate deficient wafers.

Figure 4:
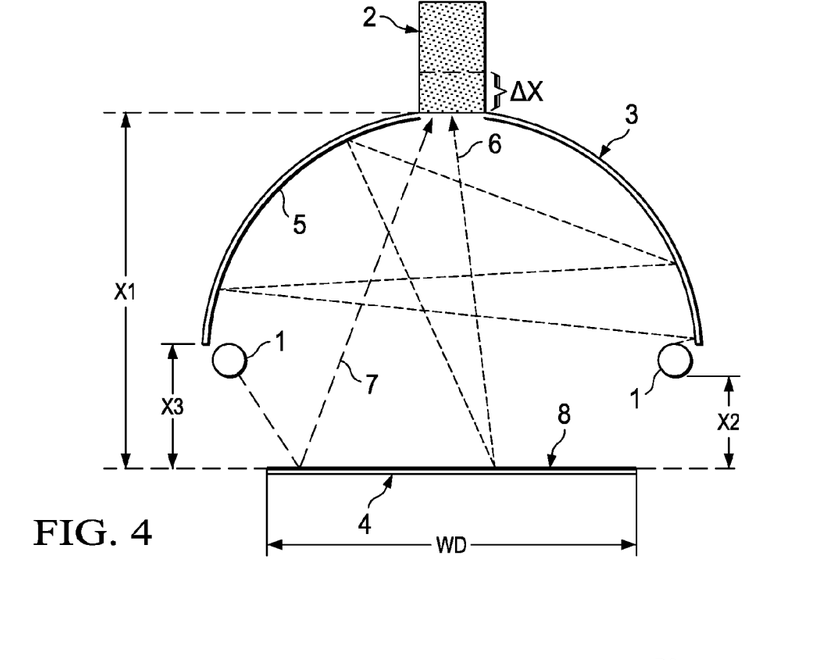
FIG. 4 shows a simplified diagram of a cross-sectional side view of an apparatus configured according to aspects of the invention.

FIG. 4 shows a cross-sectional side view of an inspection apparatus for detecting defects, which is configured in accordance with several aspects of the invention. This apparatus may be used in the inspection system 100. A planar platform 4, for example a chuck, provides a support surface onto which a semiconductor wafer 8 of diameter WD can be placed for inspection. A dome 3, a light sensor 2 (for example a CCD camera) and a light source 1 are arranged such that light from the light source 1 may be received by the light sensor 2 either after being directly reflected off the surface of the semiconductor wafer 8, or indirectly after first being reflected off the inner surface 5 of the dome 3. This is illustrated by the example light beams 6 and 7. Light beam 7 is emitted from light source 1 and directly reflected from the surface of semiconductor wafer 8 into the field of view of camera 2. Light beam 6, on the other hand, is emitted from light source 1 and reflects several times off the dome inner surface 5 before being reflected by the surface of the semiconductor wafer 8 and to the light sensor 2. Light sensor 2 can thus produce an image, which is an overlay of directly reflected light (as light beam 7) and indirectly reflected light (as light beam 6) from light source 1. Specular reflection may advantageously be avoided by providing the inner surface of dome 3 as a diffusely reflecting surface. The light beams 6 and 7 are only illustrative examples of the overlaying effect of the dome using diffusely reflected light.

From the perspective of the light sensor 2, the inner surface 5 of the dome 3 and the light source 1 are configured to effectively interact as if the inner surface were matte gray and the light source were emitting white light. A white light source 1 and matte gray surface 5 can be used in a preferred embodiment.

This basic interaction of light source and the inner surface of the dome 3 may also be described in various different ways. The inner surface 5 of dome 3 may be adapted to reflect in a non-specular (i.e., non-mirror) manner. The inner surface 5 may be adapted to absorb light uniformly across the spectrum of the light source 1. This is the effect of a gray surface 5 for a white light source 1. However, if the light source 2 emits colored light, this may be compensated by using a colored inner surface 5 or color filters in front of the light sensor 2 so as to have the combined effect of a gray surface 5 for a white light source 1.

A specific amount of light of light source 1 may be diffusely reflected. However, it may not be 100% reflective to this specific type of light (e.g., white light). Furthermore, a certain amount of light of light source 1 may be absorbed by the inner surface 5 of dome 3. Therefore, for a light source 1, which emits white light, the inner surface 5 of dome 3 may have a plain and smooth structure and gray color. In other words, the inner surface 5 of the dome 3 can emit light having a mixture of frequencies in the visible light frequency range that produce a gray color.

The light sensor 2 can be advantageously arranged to prevent light from the light source 1 from entering the light sensor 2 unless it is either or one of reflected directly off the surface of wafer 8 or indirectly reflected off the surface of the wafer 8 after first reflecting off the dome inner surface 5.

A vertical cross section of the inner surface 5 of dome 3 may have a semicircular shape. In another embodiment, it may also have a parabolic shape. Due to diffuse reflection of the inner surface of the dome, other shapes of the dome may be used which may have the same advantageous effects according to aspects of the invention. Even edges or corners in the inner surface may be tolerated to a certain extent.

The light sensor 2 may be arranged in the top center of the dome spaced by a small distance from the inner surface 5. The distance $\Delta X$ between light sensor 2 and inner surface 5 may advantageously be within a range from 0 to about 20 cm. For a camera, as for example a CCD camera being used as a light sensor, the objective lens may be included in this aspect of the invention. The dimensions for $\Delta X$ may then either relate to the front surface of the objective lens or to the position of the actual light sensor (integrated chip, capacitive array) in the camera.

The distance X1 between the light sensor 2 and the surface of the wafer 8 may advantageously be within a range of from one to three times the wafer diameter WD. This may be expressed as $WD \leq X1 \leq 3*WD$. However, even for larger wafer diameters, X1 may be chosen smaller and may lie within the following a range given by $100\ mm \leq X1 \leq 300\ mm$.

The distance X2 between light source 1 and the surface of the wafer 8 may range from one to two times the observed wafer diameter. This may be expressed as $WD \leq X1 \leq 2*WD$. However, smaller values for X1 may also be suitable as, for example, values between 20 mm and 100 m even for larger wafers having a diameter WD of more than 100 mm The distance X3 between the lower edge of the dome 3 and the surface of the wafer 8 may advantageously be within a range of from 0 and 5 cm. Greater values for X3 are also acceptable if the light distribution and reflection still achieves the desired effects. In other embodiments, the lower edge may even extend over the wafer surface. X3 would then have a negative value.

Figure 5:
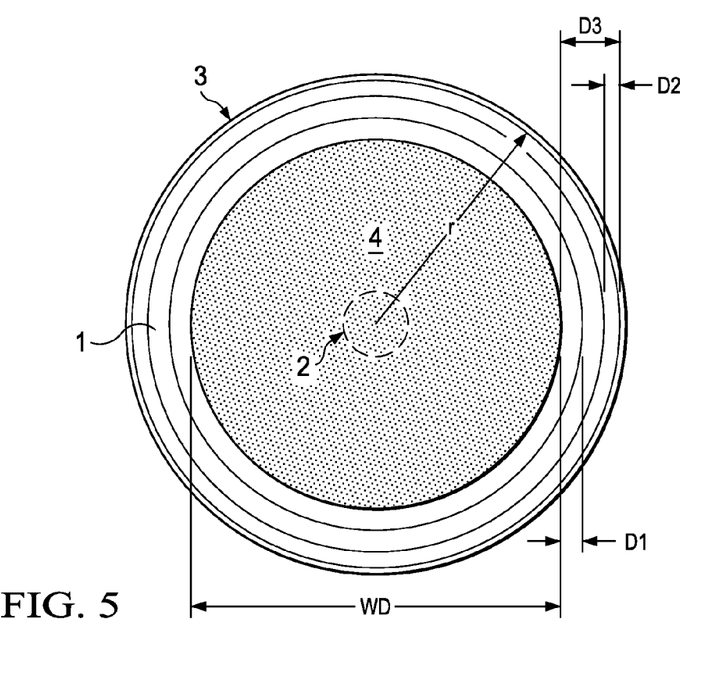
FIG. 5 shows a simplified diagram of a cross-sectional top view of an embodiment configured according to aspects of the invention.

FIG. 5 shows a cross-sectional top view of an apparatus configured according to aspects of the invention. The light source 1 is circular and encompasses the plane, for example a chuck, on which the semiconductor wafer 8 may be placed for inspection. The dome 3 is only represented by its lower edge directed to the wafer. The illustrated dome also has a circular shape. The light sensor 2 may be placed in the center of the dome 3.

The radius r of the lower edge of the dome may advantageously be within a range of from one to three times the observed wafer diameter ($WD \leq r \leq 3*WD$).

In an embodiment, the distance D1 between the circumference of the wafer 8 and the light source 1 may be within a range of from 0 to two times the wafer diameter WD ($WD \leq D1 \leq 2*WD$). In an aspect of the invention, the distance D2 between the light source and lower edge of the dome 3 may be within a range of from 0 to two times the observed wafer diameter ($WD \leq D2 \leq 2*WD$). Furthermore, in an embodiment, the distance D3 between the lower edge of the dome 3 and the wafer may be within a range of from 0 to four times the observed wafer diameter ($WD \leq D2 \leq 4*WD$).

Figure 6:
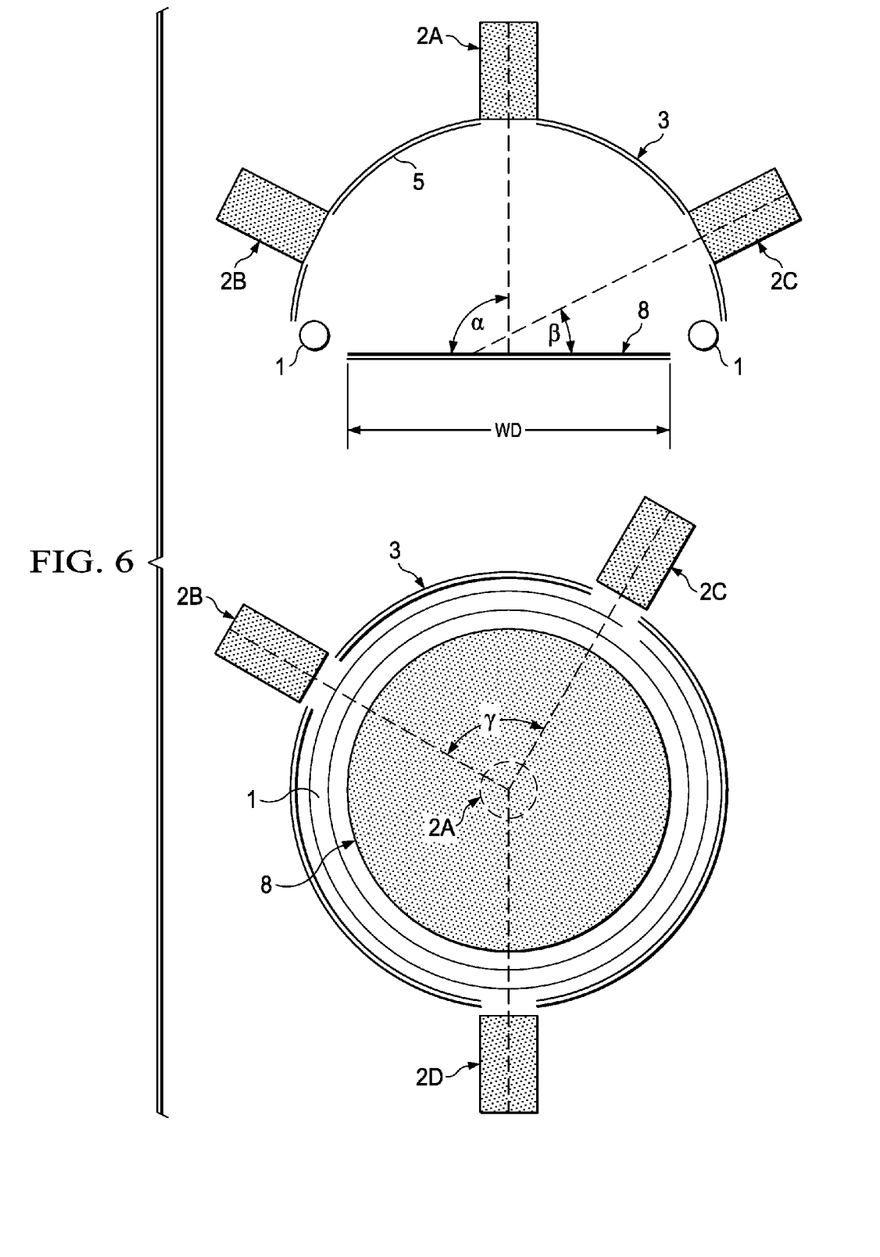
FIG. 6 shows a simplified diagram of an embodiment of the invention configured according to aspects of the invention.

FIG. 6 shows an embodiment of the invention using multiple light sensors 2A, 2B, 2C and 2D and a dome. All light sensors may be configured as explained above. Each light sensor 2A to 2D may be a CCD camera. Three light sensors 2B, 2C, 2D may be arranged with an acute angle $0° \leq \beta \leq 90°$ of view relative to the wafer surface. Advantageous embodiments may use angles within a range of $0° \leq \beta \leq 45°$, such as, for example $\beta = 10°, 20°, 30°$ or $45°$.

The multiple light sensors 2B, 2C, 2D may be spaced circumferentially about the dome 3 at angles γ with respect to each other. They may, for example, be arranged at equiangular spacings of $\gamma = 120°$ about a circular cross section of the dome 3, at equal heights and with equal viewing angles β. One light sensor 2A may be arranged in the top center of the dome 3, as shown with light sensor 2 in FIGS. 1 and 2. The angle α between the central axis of the light sensor 2A and the wafer surface may then be 90°. However, deviations from 90° may be also acceptable as long as the desired interaction of dome, light source, wafer surface and light sensor are still achieved.

Although the invention has been described with reference to details of specific example embodiments, those skilled in the art to which the invention relates will appreciate that many variations of the described embodiments and other embodiments are possible within the scope of the claimed invention.

What is claimed is:

1. Apparatus for inspecting a semiconductor wafer, comprising:
    a platform for supporting a wafer to be inspected;
    a light source;
    a plurality of light sensors;
    a dome having a convex diffusely reflecting inner surface positioned facing the platform; and
    a data processing unit;
    wherein the platform, light sensors, plurality of light sensors and dome are relatively arranged so that the light sensors can simultaneously acquire a set of images from respective different angles of view of a surface of the wafer supported on the platform and simultaneously illuminated both by hard light from the light source incident sideways on and directly reflected from the wafer without reflection from the inner surface and by soft light from the light source incident substantially uniformly from above and indirectly reflected from the wafer after being first reflected from the inner surface; and
    wherein the data processing unit is connected to the light sensors and adapted to receive data representative of the images acquired by the light sensors, to compare each image with a corresponding image of another set of images of a surface of another wafer previously acquired by the same light sensors from the same respective different angles of view, and to automatically detect a defect based on the image comparison.

2. The apparatus of claim 1, wherein the data processing unit is adapted to detect a defect requiring soft light and a defect requiring hard light.

3. The apparatus of claim 1, wherein the light source and inner surface are relatively dimensioned, configured and adapted so that light reflected off the inner surface reflects the same as white light reflected off a matte gray surface.

4. An apparatus for inspecting a semiconductor wafer, the apparatus comprising:
    a light sensor;
    a dome with a convex diffusely reflecting inner surface directed towards a platform for supporting a semiconductor wafer to be inspected; and
    a light source;
    the light sensor, dome, light source and platform being relatively configured such that the light sensor can receive both soft light from the light source that is incident substantially uniformly from above and indirectly reflected by a surface of the wafer after being first reflected by the inner surface of the dome and also hard light from the light source that is incident sideways on and directly reflected by the surface of the wafer without being first reflected by the inner surface of the dome.

5. The apparatus of claim 4, wherein the light sensor, the dome, the light source and the platform are configured, dimensioned and arranged so that light is reflected off the inner surface of the dome with the same effect as light from a white source reflected off a matte gray surface.

6. The apparatus of claim 4, wherein the light sensor is arranged at a top central position relative to the dome.

7. The apparatus of claim 6, wherein the light source is arranged between the light sensor and the platform.

8. The apparatus of claim 4, wherein the light sensor is arranged to prevent light entering the light sensor directly from the light source.

9. The apparatus of claim 4, wherein the light sensor is arranged at a central position of the dome, spaced by a distance from the inner surface.

10. The apparatus of claim 9, wherein the platform is configured for supporting a wafer of given diameter; the inner surface is a convex surface having a lower edge with a lateral dimension greater than the given diameter; and the light source is a circular neon light source of diameter greater than the given diameter and positioned peripherally of the platform, vertically between the dome and the platform.

11. A method of detecting a defect on a semiconductor wafer, the method comprising:
    illuminating a surface of a first wafer;
    simultaneously acquiring a plurality of images of the surface of the first wafer from different viewing angles;
    illuminating a surface of a second wafer;
    simultaneously acquiring a plurality of images of the surface of the second wafer from different viewing angles;
    comparing the images of the surface of the first wafer with corresponding same viewing angle images of the second wafer; and
    determining the defect based on differences identified in the comparison;
    wherein illuminating the surface of the first wafer and illuminating the surface of the second wafer comprises illuminating the surfaces both with hard light incident sideways directly from a light source without reflection off a diffusing surface and simultaneously with soft light incident substantially uniformly from above indirectly from the light source after being first reflected off a diffusely reflecting surface; and
    wherein the images acquired of the surfaces of the first and second wafers are superposed images formed by the direct and indirect light illuminations.

12. The method of claim 11, wherein illuminating the surface of the first wafer and illuminating the surface of the second wafer indirectly with soft light from above comprises illuminating the surfaces with light first reflected off the diffusely reflecting surface with the effect of white light reflecting off a matte gray surface.

13. The method of claim 11, wherein illuminating the surfaces comprises supporting the respective wafers on a platform below a dome having a diffusely reflecting inner surface directed downwardly toward the platform; and illuminating the surfaces with light from the light source that is first reflected by the inner surface and subsequently reflected by a surface of the semiconductor wafer and also with light from the light source that is directly reflected by the surface of the wafer without being first reflected by the inner surface.

14. The method of claim 13, wherein acquiring the pluralities of images comprises acquiring the images by a light sensor formed by the direct and indirect illuminations without light entering the light sensor directly from the light source.

15. The method of claim 14, wherein the images are acquired by a light sensor arranged at a central position of the dome, spaced by a distance from the inner surface.

16. The method of claim 15, wherein the platform is configured for supporting a wafer of given diameter; the inner surface is a convex surface having a lower edge with a lateral dimension greater than the given diameter; and the light source is a circular neon light source of diameter greater than the given diameter and positioned peripherally of the platform, vertically between the dome and the platform.

* * * * *